(12) United States Patent
Helikar et al.

(10) Patent No.: US 9,405,863 B1
(45) Date of Patent: Aug. 2, 2016

(54) SYSTEM AND METHOD FOR DYNAMIC MODELING OF BIOCHEMICAL PROCESSES

(71) Applicant: The Board of Regents of the University of Nebraska, Lincoln, NE (US)

(72) Inventors: Tomas Helikar, Omaha, NE (US); Jim Rogers, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 768 days.

(21) Appl. No.: 13/648,807

(22) Filed: Oct. 10, 2012

Related U.S. Application Data (60) Provisional application No. 61/545,425, filed on Oct. 10, 2011.

(51) Int. Cl.
G06G 7/58 (2006.01)
G06F 17/50 (2006.01)
G06F 19/12 (2011.01)

(52) U.S. Cl.
CPC ............ G06F 17/5009 (2013.01); G06F 19/12 (2013.01)

(58) Field of Classification Search
CPC ...... G06F 19/16; G06F 19/3437; G06F 19/12
USPC ...................................... 703/2, 11
See application file for complete search history.

(56) References Cited

U.S. PATENT DOCUMENTS

| | | | |
|---|---|---|---|
| 6,983,227 B1 | 1/2006 | Thalhammer-Reyero | |
| 8,046,174 B2 | 10/2011 | Li | |
| 2002/0091666 A1 | 7/2002 | Rice | |
| 2003/0018457 A1 | 1/2003 | Lett | |
| 2003/0113761 A1 | 6/2003 | Tan | |
| 2004/0133355 A1 | 7/2004 | Schneider | |
| 2005/0065767 A1 | 3/2005 | Arnstein | |
| 2009/0138415 A1 | 5/2009 | Lancaster | |
| 2010/0285082 A1 | 11/2010 | Fernandez | |
| 2011/0307182 A1 | 12/2011 | Ludwig | |

FOREIGN PATENT DOCUMENTS

| WO | PCTUS00/03318 | * | 8/2000 | ............. G06F 19/12 |
|---|---|---|---|---|

OTHER PUBLICATIONS

Ethan G. Cerami et al.,"cPath: Open Source Software for Collecting, Storing, Querying Biological Pathways", BMC Bioinfomiatics, Nov. 13, 2006, p. 1-9, 7:497, BioMed Central Ltd.

Bree B. Aldridge et al., "Physiochemical Modeling of Cell Signalling Pathways", Nature Cell Biology, Nov. 2006, p. 1195-1203, 8:11, Nature Publishing Group, Boston, MA.

Robert C. Gentleman et al., "Bioconducor: Open Software Development for Computational Biology and Bioinformatics", Genome Biology, Sep. 15, 2004, Article R80, 5:10.

"In silico simulation of molecular biology experiments", University of the Basque Country Country, 1 pg.; 2012.

* cited by examiner

*Primary Examiner* — Hugh Jones
(74) *Attorney, Agent, or Firm* — Tyson B. Benson; Advent, LLP (57) ABSTRACT

Aspects of the disclosure pertain to a system and method for dynamic modeling of biochemical processes. The system and method allow for the models to be created collectively by the world-wide scientific community, while also providing a user-friendly system/method for promoting ease of building, simulation and analysis of the models.

20 Claims, 4 Drawing Sheets

SYSTEM AND METHOD FOR DYNAMIC MODELING OF BIOCHEMICAL PROCESSES

CROSS-REFERENCE TO RELATED APPLICATIONS

This application claims priority to U.S. Provisional Application No. 61/545,425 filed on Oct. 10, 2011, which is hereby incorporated by reference in its entirety.

BACKGROUND

Biochemical pathways are studied in order to learn about the behavior of the cell. These pathways form networks that are complex, diverse and dependent upon each other. In order to fully understand the cell, knowledge of all of these pathways and how they interrelate is necessary.

SUMMARY

This Summary is provided to introduce a selection of concepts in a simplified form that are further described below in the Detailed Description. This Summary is not intended to identify key and/or essential features of the claimed subject matter. Also, this Summary is not intended to limit the scope of the claimed subject matter in any manner Aspects of the disclosure pertain to a system and method for dynamic modeling of biochemical processes. The system and method allow for the models to be created collectively by the world-wide scientific community, while also providing a user-friendly system/method for promoting ease of building, simulation and analysis of the models.

BRIEF DESCRIPTION OF THE DRAWINGS

The numerous advantages of the present invention may be better understood by those skilled in the art by reference to the accompanying figures in which.

DETAILED DESCRIPTION

Aspects of the disclosure are described more fully hereinafter with reference to the accompanying drawings, which form a part hereof, and which show, by way of illustration, example features. The features can, however, be embodied in many different forms and should not be construed as limited to the combinations set forth herein; rather, these combinations are provided so that this disclosure will be thorough and complete, and will fully convey the scope. Among other things, the features of the disclosure can be facilitated by methods, devices, and/or embodied in articles of commerce. The following detailed description is, therefore, not to be taken in a limiting sense.

Overview

As early as seventy years ago, biomedical research scientists were able to study biochemical pathways and make great progress in understanding the fundamental workings of the cell. By the 1970s, it did not appear to be unreasonable to extrapolate that rate of discovery and be hopeful that all aspects of the cell would be understood within a generation. Unfortunately, that promise of quick understanding of cellular processes has not been truly fulfilled. As our understanding of new types of biochemical pathways increases, it is clear that they form networks of astonishing complexity and diversity. This means that a system of complex pathways involved in regulation of one area of the cell (which are so complex a researcher could spend their entire career working in that area alone) is intricately interconnected with systems of complex pathways involved in regulation of other, equally complex areas of the cell. Thus, all of these pathway systems must be studied together and understood in order to fully understand the cell.

As more fully set forth below, aspects of the disclosure include a system and method for providing dynamic modeling and simulation of biochemical processes. The system is a platform that incorporates information on biochemical pathway dynamics which allows scientists to create a community-based model which they can put into motion to observe the behaviors of the various pathway systems within the context of the whole cell. The platform includes a core repository of information necessary for dynamic modeling and allows any user in the community to download the core model and change any aspect of it based on that user's insights from his/her area of expertise. Any positive changes could then be considered for addition to the core model. In this way, the system disclosed herein allows a dynamical model of any biological or biochemical network process to be created by a world-wide community of experts. Further, the system disclosed herein allows for biologists to build and modify large-scale computational models in an intuitive and non-mathematical fashion.

The System

Figure 1:
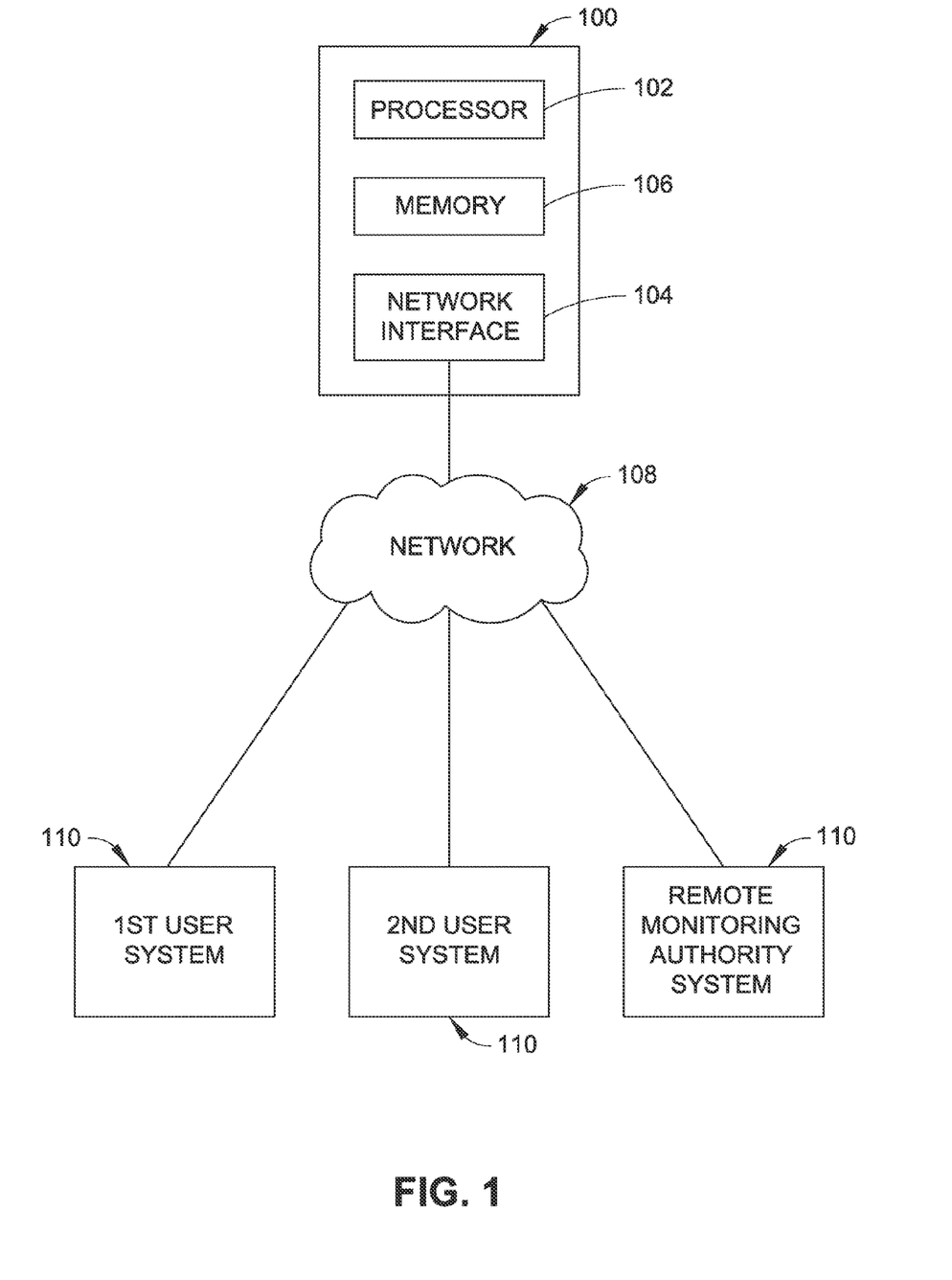
FIG. 1 is an example conceptual block diagram schematic of a system for providing dynamical modeling of biochemical processes, the system shown being connected to a plurality of external entities over a network.

As indicated in FIG. 1 (FIG. 1), a system 100 (e.g., Cell Collective) for dynamic modeling of biochemical processes is shown. In embodiments, the system 100 is a computer which includes a processor 102, a network interface 104 and a memory 106. The processor 102 provides processing functionality for the system 100 and can include any number of processors, micro-controllers, or other processing systems and resident or external memory for storing data and other information accessed or generated by the system 100. The processor 102 can execute one or more software programs that implement techniques described herein. The processor 102 is not limited by the materials from which it is formed or the processing mechanisms employed therein and, as such, can be implemented via semiconductor(s) and/or transistors (e.g., using electronic integrated circuit (IC) components), and so forth.

The network interface 104 is operatively configured to communicate with components of the system 100. For example, the network interface 104 can be configured to transmit data for storage in the system 100, retrieve data from storage in the system 100, and so forth. The network interface 104 is also communicatively coupled with the processor 102 (e.g., to facilitate data transfer between components of the system 100 and the processor 102). The network interface 104 provides functionality to enable the system 100 to communicate using one or more networks. In implementations, the network interface 104 can include a variety of components including, but not necessarily limited to: cellular telephone transceivers, modems, routers, wireless access points, and so forth, and associated software employed by these components (e.g., drivers, configuration software, and so on). In FIG. 1, the network interface 104 is illustrated as a component of the system 100. However, one or more components of the network interface 104 can be implemented as external components communicatively coupled to the system 100 via a wired and/or wireless connection.

The network interface 104 can be configured to connect to a network 108. The network 108 can assume a wide variety of configurations. For example, the network 108 can comprise, but is not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to be restrictive of the present disclosure. Further, the network 108 can be configured to include a single network or multiple networks across different access points. The system 100 can also comprise and/or connect to one or more input/output (I/O) devices (e.g., via the network interface 104) including, but not necessarily limited to: a display, a mouse, a touchpad, a keyboard, and so on.

In implementations, the network interface 104 can be used to communicatively couple the system 100 to one or more external entities 110. For example, the network interface 104 can be used to connect the system 100 to a remote monitoring authority and/or other computer systems 110. The memory 106 is an example of tangible computer-readable storage medium that provides storage functionality to store various data associated with operation of the system 100, such as software programs and/or code segments, or other data to instruct the processor 102, and possibly other components of the system 100, to perform the steps described herein. Although a single memory 106 is shown, a wide variety of types and combinations of memory can be employed. The memory 106 can be integral with the processor 102, can comprise stand-alone memory, or can be a combination of both. The memory 106 can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, and so forth. In embodiments, the memory 106 can include removable integrated circuit card (ICC) memory, such as memory provided by a subscriber identity module (SIM) card, a universal subscriber identity module (USIM) card, a universal integrated circuit card (UICC), and so on.

Figure 2:
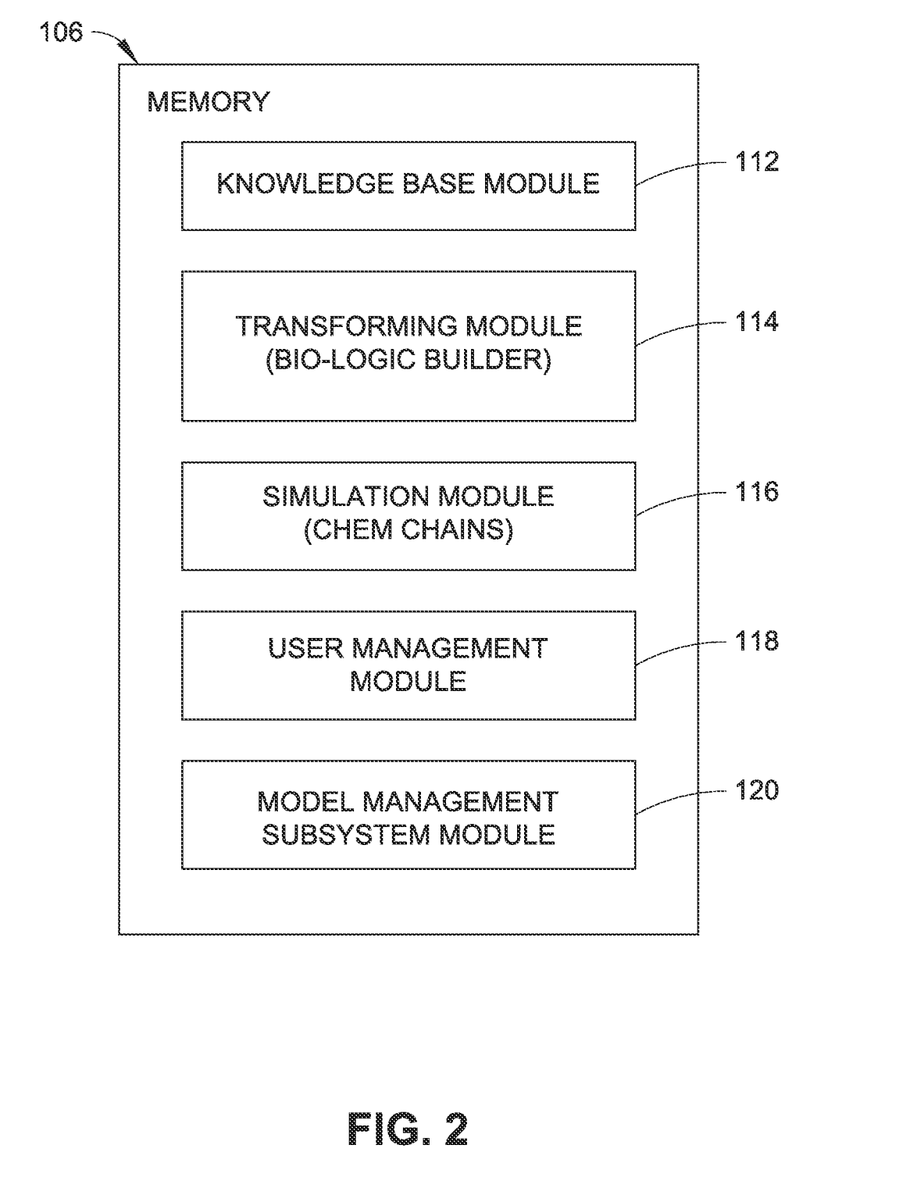
FIG. 2 is an example conceptual block diagram of modules of a memory of the system shown in FIG. 1.

In embodiments, the system 100 is a web-based platform via which laboratory scientists can collaboratively build mathematical models of biological processes by utilizing existing laboratory Static Laboratory Data As indicated in FIG. 2 (FIG. 2), the memory 106 of the system 100 includes a plurality of modules for facilitating the provision of the herein described functionality of the system 100.

In embodiments, the memory 106 includes a first module, the first module being a data module (e.g., a laboratory data module, a static laboratory data module, a knowledge base) 112. The first module 112 is configured for providing an environment for laboratory scientists to contribute information about specific biological interactions. The environment provided by the first module 112 allows users to add their information to the system 100 in an interactive and collaborative fashion. In embodiments, the first module (e.g., platform) 112 is organized by pages, such that each page is dedicated to a single biological species. For example, a scientist working on the regulatory mechanism of the Erk MAP kinase can add their data to a page dedicated to this kinase, and can discuss with other Erk specialists how their findings fit in the big picture (e.g., within the model as a whole). Because the data and information necessary to build the subsequent mathematical representation does not require any quantitative parameters, but instead only qualitative relationships (e.g., Erk is activated by MEK), the process of contributing, discussing and modifying this information is straightforward.

When laboratory scientists produce new results, for example, regarding the role of one protein interacting with another protein, these results are usually published along with thousands of other results generated by the scientific community. The knowledge base module 112 allows laboratory scientists to contribute to the integration of knowledge about individual biological processes at the most local level which includes, for example, the identification of direct protein-protein interactions. The system (e.g., platform) 100 allows for extension of static knowledge/data into dynamical models. Thus, the information provided (e.g., stored) in the knowledge base module 112 is dynamical. This means that the information (e.g., which is purely qualitative) contained in the knowledge base module 112 takes into account the dynamical relationship between all interacting partners of a biological process. For example, if species Z has two positive regulators (e.g., X and Y), the dynamical information would indicate whether X and Y are both necessary for activation of Z, or whether either X or Y alone is sufficient to activate Z. This is the type of information that is used to construct dynamical models via the system 100.

As described above, the knowledge base module 112 allows laboratory scientists to collaboratively contribute their knowledge to/of the complete regulatory mechanisms of individual biological species. Because all of the regulatory information forms the basis of the computational model and thus, must be correct for the model to exhibit similar behaviors as seen in the laboratory, this process of aggregating all known information about a species into one place can also serve as a mechanism to identify possible contradictions or holes in the current knowledge about the regulatory mechanism of a particular species. For instance, using the example set forth above, assuming laboratory scientist A discovers that proteins X and Y are both necessary to activate species Z, but scientist B's laboratory results suggest either protein X or Y can sufficiently activate Z, the process of integrating all known information about species Z becomes crucial in discovering such discrepancies (or additional missing information), which may not have been found otherwise. Because a goal of the system 100 is to integrate this information into dynamical models, simulations of the large-scale model (which might have hundreds or thousands of additional components in it) can suggest whose data is more likely to be correct. Assuming that when scientist A puts his information into the model, the model exhibits phenomena similar to what is seen in the laboratory, and that when scientist B puts his information into the model, the model exhibits simulation dynamics which fail to resemble known actions of the real system, new laboratory experiments with a potential to produce more insights into the regulatory mechanism of protein Z would be warranted. The system 100 allows for experimental data to be seen within and re-integrated into the context of the entire system (e.g., cell system) to promote full understanding of very complex biological systems and how they work.

As mentioned above, the knowledge base module 112 includes a dedicated page for each species where laboratory scientists can directly deposit their knowledge regarding the species' regulatory mechanisms. While the knowledge base module 112 gives users the ability to input their data in a free form which can also be interactively discussed, each page is structure to help users organize and review their data more efficiently. In embodiments, each page includes a regulation mechanism summary section which describes the general mechanism of the activation/deactivation of the species. This section is most important from a systems perspective as the information therein takes into account the role of all immediate upstream regulators.

In embodiments, each page includes an upstream regulators section which contains the list of key players that have a role in the regulation of the species, as well as any evidence (as found in the laboratory) supporting those roles. Using the earlier example involving the regulatory mechanism of species Z, this section would include proteins X and Y as upstream regulators and the findings of laboratory scientists A and B suggesting the role of these regulators in the activation of the species. Further, the regulation mechanism summary section would contain the overall dynamical information as to how Z is regulated in the context of both X and Y (e.g., are both regulators required for activation, or only one of them?).

In embodiments, each page includes a model-specific information section. The model-specific information section can be used by users to define upstream regulators and the regulation mechanism summary that is specific to users' different models. For example, the regulation mechanism summary of species Z in scientist A's model would describe his findings that both upstream regulators of Z are necessary for its activation, whereas scientist B's regulation mechanism summary on the page for species Z would indicate that either one of the upstream regulators can activate Z. Further, because a number of molecular species can be regulated differently based on the type of cell, this section allows users to enter such cell type-specific information. For example, an intracellular species can be regulated either by different players, or the same players but within different dynamical relationship in, for instance, a T cell and a mammary epithelial cell. The model-specific information section enables users to differentiate between the regulatory mechanisms of the species in the two (or more) different types of cell as depicted via different models.

In embodiments, each page includes a references section. The references section can be used by users to record any published works that support information entered in any of the above sections. Users can enter references in the references section by simply entering an identification (e.g., Pubmed ID (pmid)) or manually entering information for an article of interest and the system 100 is configured for automatically importing bibliographical information about the article.

In embodiments, the knowledge base module 112 includes biological knowledge/information describing model(s) of signal transduction. For example, dynamical information about hundreds of biochemical interactions between species, including a number of main signaling pathways (e.g., Epidermal Growth Factor, Integrin and G-Protein Coupled Receptor pathways) can be deposited and stored within the knowledge base module 112. Once the dynamical information about individual interactions is added to the knowledge base module (e.g., platform) 112, the next step is to convert this knowledge into a dynamical model (e.g., a virtual cell) which can be simulated and analyzed on a computer, which will be discussed below.

Transformation of the Static Data into a Dynamical Model

In embodiments, the memory 106 includes a second module (e.g., a transformation module, Bio-Logic Builder) 114. The second module 114 is configured for converting static information (e.g., laboratory data) into a mathematical model of which the dynamics can be viewed via simulation. The second module 114 identifies building blocks (e.g., bio-logic gates) of biological processes. The building blocks have a specific mathematical representation, but to the user (e.g., a biologist), they appear as simple black boxes which can be manipulated without requiring knowledge of the details of the underlying mathematics.

The main principle of biochemical processes such as signal transduction is the ability of a biochemical species (e.g., a protein) to transduce a signal to another biochemical species. This process can happen via multiple mechanisms, ranging from a simple binding of the signaling elements to post-translational modifications (e.g., phosphorylation, methylation, etc.). However, for purposes of mathematical abstraction, this action can be expressed as an activation of one element by another. The reverse of this, namely, to prevent or stop a signal from being passed, is deactivation or inactivation. In terms of protein-protein interaction, if a protein causes its downstream target to be activated, the protein can be referred to as a positive regulator and if a protein results in the deactivation of that target, the protein can be referred to as a negative regulator. These two types of regulators are a way in which laboratory scientists express these interactions, making them an ideal basis for the building blocks (e.g., bio-logic gates).

The use of activation and deactivation to describe interactions of a dynamical system of interacting elements is simple and beneficial. These so-called logical models benefit from the fact that the individual interactions are easy to describe and understand, and have the added benefit that they are not required to be parameterized. This is advantageous because values of parameters (e.g., rate constants) are generally not known in the cell. Logical models can be successfully used to model a number of complex biochemical systems, such as: the yeast cell cycle, the mammalian cell cycle, the human cholesterol biosynthesis pathway, cellular signal transduction networks in plant guard cells, T cells, the ErbB signaling network and multiple, interacting signaling pathway families in the fibroblast cell.

In embodiments, the second module 114 (e.g., transformation module) includes a web-based logic generator (e.g., Bio-Logic Builder). Bio-Logic Builder 114 automatically generates a logical relationship between complex interaction partners, thereby organizing all the myriad (e.g., millions of) activation/deactivation relationships in a large-scale model. Bio-Logic Builder 114 makes the system 100 easily accessible to laboratory research scientists by allowing them to perform high-level modeling without requiring them to have knowledge of quantitative methods.

The second module 114 includes a web-based software tool that allows laboratory scientists to define mathematical representations of biological regulatory mechanisms in an intuitive and modular fashion. As part of the user interface of tool, generalized bio-logic modules are defined to provide users with the building blocks for many biological processes. To build/modify computational models using these building blocks, biologists provide purely qualitative information about particular regulatory mechanisms (as is generally found in the laboratory) without requiring users to become mathematicians or computer scientists. The user interface captures a novel algorithm which allows users to build interactions between a number of species in a qualitative and highly modular fashion. Bio-Logic Builder 114 provides users with building blocks of two types. First, users can define modules corresponding to positive and/or negative regulators that are involved in a given biological interaction (e.g., kinase X phosphorylates and activates protein Y, as is the case in studies of biochemical signal transduction). Because only few biological interactions can be represented as simple positive and/or negative regulators, users can specify a second type of bio-logic modules. This second type of bio-logic modules (e.g., conditions and subconditions) correspond to elements in biological processes such as co-factors. While Bio-Logic Builder 114 is a web-based software tool, the mathematical functions created by the software in the background can be easily saved and plugged into any simulation/analysis software supporting discrete (e.g., Boolean) frameworks, such as ChemChains.

In embodiments, once a user defines the regulatory mechanism of a biological species of interest, Bio-Logic Builder 114 generates the corresponding mathematical function in the form of a Boolean function. The regulatory mechanism of any species defined in Bio-Logic Builder 114 can be saved and downloaded on user's computer 110 in a number of formats, including a tab-delimited csv file as a truth table, text file with Boolean expressions, and an Extensible Markup Language (XML) file (e.g., Systems Biology Markup Language; SBML). The Boolean function generated by Bio-Logic Builder 114 can be subsequently read and evaluated by a simulation software tool (e.g., ChemChains)

To provide an intuitive and user-friendly graphical user interface (GUI), Bio-Logic Builder 114 is designed for users to interact with it in a qualitative and modular fashion, similar to the way many biological regulatory mechanisms are elucidated in the laboratory. While many of these mechanisms include a number of different biochemical reactions between any two species, these reactions can be largely abstracted to a higher layer and generalized as either positive or negative. A positive reaction would be one in which an upstream regulator positively affects the activity of (e.g., activates) its effector. A negative reaction corresponds to an inhibitory relationship between two biological species. The main idea behind the user interface of Bio-Logic Builder 114 is basic differentiation between positive and negative regulators involved in the regulatory mechanism of a given species. This differentiation and the natural modularity of biological regulatory mechanisms is translated into Bio-Logic Builder 114 by allowing users to define positive and negative modules (i.e., bio-logic gates) of the mechanism under a positive regulation center and a negative regulation center respectively.

Many biological activating and inhibitory functions are dependent on the presence or absence of additional regulatory components. For example, the activation of phospholipase D (PLD), an important regulatory component of a number of cellular processes such as the actin cytoskeleton and receptor signaling is mediated by several signaling components such as protein kinase C or members of the ARF and Rho families. These regulators of PLD are considered positive regulators. However, in addition to these activators, the ability of PLD to fully function depends on an additional regulatory component—phosphatidylinositol 4,5-bisphosphate (PIP2)—which binds to the pleckstrin homology (PH) domain of PLD1. Therefore, the aforementioned positive regulators of PLD are accompanied by an additional signaling co-factor. Because a large number of molecular species are governed by complex regulatory mechanisms, dependent on multiple co-factors, the previously discussed generalization to only positive and negative regulators becomes over-simplistic. To address this biological reality, Bio-Logic Builder 114 allows users to define additional bio-logic gates, conditions and subconditions that can accompany each positive and negative regulation module. Conditions allow users to describe regulatory mechanisms in which the effects of one or more positive and/or negative regulators depend on an additional regulators step (e.g., localization, priming, etc.) and hence, the activation state or presence (or absence) of an additional regulator (or group of regulators). As a result, the users can define complex positive and negative regulatory modules much in the same way that biological data and knowledge are discovered in the laboratory. Once the user specifies all positive/negative regulatory modules of the mechanism, a summary page can be displayed.

As mentioned above, Bio-Logic Builder 114 can be accessed via a web browser of a user system 110. A first screen may inquire the name of the species for which the regulatory mechanism will be built. A second screen may allow the user to choose whether to start building the regulatory mechanism by specifying either the positive or negative regulation modules. The order in which the user starts does not result in a different output.

As mentioned above, the negative regulation center is where users designate upstream regulation modules that have a negative (i e, inhibitory) effect on the species of interest. A species palette section of a screen (e.g., screenshot, webpage) may be available to the user throughout the entire building process so that new species can be added/edited as needed. By default, the species for which the regulatory mechanism is being built is automatically added to the palette. Before the user can designate species as negative regulators, the species need to first be added to the species palette. Specifying a species as a negative regulator is as simple as drag-and-dropping a species from the palette into the box in a main window.

Once negative regulation modules are designated, any necessary conditions can be specified. Conditions allow biologists to specify regulatory scenarios under which a particular upstream regulator is dependent on the activity state of another species (e.g., a co-factor). Conditions for each of the negative regulation modules are defined under their respective centers. In embodiments, a conditions page is accessible from a negative center page or positive regulation center page by clicking on the center of the negative (or positive) regulation module for which conditions need to be added/modified. In embodiments, users can define conditions as IF/WHEN and UNLESS statements to define scenarios when the effects of the regulator for which a condition is being specified depend on the activity state of another biological species. Further, to promote user convenience, each condition can be annotated to reflect its biological meaning and context. Any number of conditions and subconditions can be associated with any regulator, allowing for the definition of the most complex regulatory mechanisms. The user can then be presented with a menu option to allow a user to make an entry indicating that the user wishes to navigate away from the negative regulation center and to a center home page where the positive regulation center can be selected.

Positive regulation modules of the species of interest are specified in the positive regulation center. Once species are added to the species palette, they can be defined as positive regulation modules in a similar fashion as was done with the negative regulation modules. Subconditions can be specified after selecting (e.g., clicking) a subconditions menu option (e.g., button) on the condition page of the regulation module center.

Once all negative and positive regulation modules are defined, the user can be directed to the next screen, the dominance page. On the dominance page, users can define the strength of each negative module in terms of how dominant it is over the individual positive regulation modules. A negative module dominant over all positive regulators (pre-selected by default) has the largest negative effect on the state of the species of interest, whereas a negative module dominant over none of the positive modules will have no effect on the activity of the species.

Once the strength of the negative regulation modules is selected, the system 100 is configured for allowing the user to specify the final component of the regulatory mechanism building process—the state (Active/Inactive) of the species in the case where none of the positive or negative modules are active or present in the cell (e.g., model). Upon the last page and component of Bio-Logic Builder 114, the user can navigate to the summary page. This page displays all regulatory modules involved in the regulatory mechanism of the species of interest. The program builds the mathematical function based on the regulatory modules specified by the user in the background. The generated function can then be plugged into a larger model and simulated/analyzed by one of the previously mentioned simulation software tools (e.g., Chem-Chains), which can directly support logical models represented as Boolean functions and can be used to easily simulate models created with Bio-Logic Builder 114.

In Bio-Logic Builder 114, the head regulators represent the main positive/negative regulation modules, within which conditions and subconditions are subsequently added. When a number of regulation species appear to be conceptually equal, Bio-Logic Builder 114 requires that one of these species be selected as the head regulator, whereas the others are considered as (sub)condition(s). Fortunately, because of the mathematical relationship between the head regulators and the conditions, the mathematical representation of the interaction will be the same in both cases. Such a scenario requires a user to use their discretion and decide how to represent the regulatory mechanism. Given a unique combination of user inputs, the algorithm underlying Bio-Logic Builder 114 will cause Bio-Logic Builder 114 to generate a predictable, but not globally unique result.

Defined regulators and their relationships are converted by Bio-Logic Builder 114 into Boolean functions. All main positive/negative regulators are defined as independent modulators of the given species. Hence the Boolean function is constructed as a Boolean expression by concatenating all positive regulators using the Boolean OR operator. As also illustrated in the figure, negative regulators defined in the Bio-Logic Builder 114 are then appended (AND'ed) in a negated form to the positive regulators. The set of negative regulators (NR) that is appended to each individual positive regulator (PR) is determined by the dominance of the corresponding negative regulator selected by the user. For example, if NR1 and NR2 are specified to be dominant over PR1, the corresponding part of the Boolean expression will be the following: (P R1 $\wedge$ $\neg$(N R1 $\vee$ N R2)) . . . . If NR3 is specified as the only negative regulator dominant over PR2, the Boolean expression will be constructed as: (P R2 $\wedge$ $\neg$(N R3)).

Each positive or negative regulator can have n conditions. Each condition is constructed as a Boolean expression substring which is subsequently appended (AND'ed) to the positive or negative regulatory element. Furthermore, each condition can have m subconditions. Similar to the conditions, each subcondition is a Boolean expression substring that is appended (AND'ed) to the corresponding condition. When defining a condition or subcondition, multiple regulators may be specified. In this case, the user must specify the relationship between the regulators. This may be co-operative or independent. In a co-operative relationship, the elements are combined with the AND operator, whereas in an independent relationship, the elements are combined with the OR operator. As mentioned in the Conditions and subconditions section above, multiple (sub)conditions can be defined. Similar to having multiple components for each (sub)condition, the user must specify the co-operative or independent relationship for the (sub)conditions that are subsequently combined to the corresponding Boolean expression.

Each (sub)condition is defined by combining the "IF/WHEN" or "UNLESS" statements with a list of regulators that are specified as either Active or Inactive. In terms of a Boolean expression, the specifying IF/WHEN Inactive or UNLESS Active for a given (set of) regulators corresponds to the Boolean NOT operator. (As mentioned above, multiple (sub)condition regulators are defined, the user must specify whether the regulators are co-operative or independent. For example, the condition "IF/WHEN A, B, C ARE OFF" (A, B, and C are co-operative regulators) corresponds the following Boolean expression: ($\neg$ A $\wedge$ $\neg$ B $\wedge$ $\neg$ C). Also, "UNLESS A B C IS ON" (A, B, and C are independent regulators) is interpreted as: ($\neg$ A $\vee$ $\neg$ B $\vee$ $\neg$ C).

In embodiments, Bio-Logic Builder 114 can be configured for converting mathematical representations of network models and building any new models created via the system 100 as C++ source code (i.e., a program writing another program). This code will then be compiled (as any C++ code) and loaded as a dynamic library by a model manager component of the dynamic analysis tool (e.g., ChemChains) 116 for handling the activation and proper execution of each model. There are several advantages using this computational approach. Among them are faster and more efficient model executions and analyses. Also, the model, in the form of a C++ dynamic library, can be easily shared and executed by other simulation tools, making dissemination of the models easier. Once bio-logic is defined for all species in a given virtual cell, in silico analyses can be conducted, as will be discussed below.

Simulation and Analysis of the Dynamical Model

Once a mathematical representation of the biological structure is in hand, the biochemical system can be put into motion by a third module (e.g., simulation and analysis of dynamics module) 116 of the memory 106. The third module (e.g., platform) includes an open source software tool which is a logical model simulation and analysis tool (e.g., Chem-Chains) which allows interaction with the logical model in a continuous fashion via a graphical user interface of the system 100. For example, while individual interactions of elements (e.g., proteins) are described as activated or inactivated in logical model language, the simulation and analysis tool (e.g. ChemChains) 116 adds the ability for users to obtain (e.g., view) information about intermediate states (e.g., partial activation) of any species over time. It achieves this by allowing the user to see a Percent ON value of any species in a biochemical network at any time. The simulation and analysis tool (e.g., ChemChains) 116 is configured for successfully modeling very large and complex biological/biochemical networks, with the data generated by the models (e.g., input/output relationships) being continuous.

The simulation and analysis tool (e.g., ChemChains) 116 is further configured for providing powerful analysis that can be performed by running automated experiments in which users can simulate their models under many (e.g., tens of thousands) of randomly generated external conditions. An available patterns extension of the simulation and analysis tool (e.g., ChemChains) 116 categorizes each simulation and a specified group of output species into discrete groups, representing global responses (e.g., patterns) based on their activity level. Each pattern is then represented by an average output vector and an associated average external species vector, which provides a quick way to learn about how a model responds to certain set(s) of stimuli and maps to a specific response, an important feature to aid the understanding of how complex biological structures function and improve the development (and efficiency) of treatments for diseases associated with these systems. The output of the simulation tool (e.g., ChemChains) is interactively visualized in the user interface of the system (e.g., Cell Collective) 100. Further, users can use the software output to easily verify how well the activity levels of the specified species fit the available laboratory empirical data (e.g., the effects of receptor activation on the activity of a protein in a different area of the biochemical network). This presents to users a novel tool to obtain insight about unavailable regulatory information, which can be confirmed or rejected by controlled laboratory experiments.

The idea behind abstracting biological processes as computational models is to be able to visualize the dynamics of these processes on the computer, and to conduct in silico experiments that can provide: i) new insights into laboratory experiments; and ii) additional basis for theoretical computational research to further elucidate the complexity governing these biological processes. With its simulation and analysis component, the system 100 is configured for providing exactly these features. In embodiments of the system (e.g., platform) 100, two tools for simulations and analyses are available. As discussed above, the third module (e.g., ChemChains) 116 of the memory 106 provides the simulations and analyses tools. The real-time simulation features provided by the third module (e.g., ChemChains) 116 allows users to visualize the dynamics of any model in real time. The simulation features are designed with simplicity and intuitiveness in mind.

The simulation and analysis tool (e.g., ChemChains) 116 utilizes the concept of Percent ON, as discussed above, to allow users of the system 100 (e.g. platform) to conduct real-time simulations. Further, the simulation and analysis tool (e.g., ChemChains) 116 allows laboratory scientists to conduct many what-if scenarios in real-time. All virtual cells in the system 100, represented by species that make up the internal machinery of the cell, are simulated in extracellular environments which drive the dynamics of the cell. This environment is represented by external species corresponding to various extracellular signals such as growth hormones, stress, etc. As mentioned above, users can provide an input (e.g., via a user interface) to change the amount of each extracellular signal (e.g., measured in Percent ON on a scale of 0 to 100) and visualize the effects of the changes on the dynamics of the cell while the simulation is running. In the user interface of the system 100, a user can specify an activity level of one or more species of the biochemical network (e.g., measured by Percent ON of that species), including an external species. The activity level can be specified by the user via a real-time simulation screen (e.g., via user manipulation of a slider of the real-time simulation screen). For example, users can see how a change in the activity of ligands, expression of various receptors. In addition, by using the "Mutate" button, users can simulate the effects of gain/loss-of-function mutations on the dynamics of the various components of the users' model. For users' convenience, real time simulations can be paused and resumed at any time.

Laboratory studies to identify functional relationships between extracellular stimuli and various components of the cell involve a number of experiments that can be both time consuming and resource demanding. For example, a laboratory study that suggests that Akt (a serine/threonine kinase involved in the regulation of a variety of cellular responses such as apoptosis, proliferation, etc.) is activated in response to the Epidermal Growth Factor (EGF), the activity of Akt is measured and compared in untreated cells and cells treated with EGF. Such studies usually involve a construction of a number of protein constructs, cell cultures, assays, etc., amounting to the use of many resources. While Akt has been known for many years to be activated in response to EGF, there are many areas of the cell that are not as well understood. Laboratory experiments in such areas can be sometimes based on less sound hypotheses that may lead to the waste of many resources. The system 100 described herein allows for the ability to pre-test lab hypotheses on a computer, using a computational model, in a matter of minutes, thereby allowing laboratory scientists to weed out weak hypotheses while focusing on the ones that have a better chance of being proven correct, hence resulting in more efficient studies. This is where the dynamic analysis simulation feature provided by the third module (e.g., ChemChains) 116 comes into play. This feature/tool allows users to conduct in silico experiments that closely resemble the way laboratory experiments are performed, with the advantage that in these computational studies, researchers can perform more simulations and experiments in a much shorter time frame. For example, virtual cells in the system (e.g., cell collective) 100 can be simulated and their dynamics visualized and analyzed in hundreds of thousands of extracellular environments (as opposed to the mere treated versus untreated scenarios done in the laboratory) in a matter of minutes.

To demonstrate how the software of the system 100 can be used to perform a dynamical analysis studies, a dynamical analysis study of the relationship between EGF and Akt discussed herein. The dynamical analysis studies are done in two parts. First, on a main page of the simulation tool, users define the extracellular environment under which the study will be done. This is analogous to the preparation of cell media in the laboratory. Similar to laboratory experiments with real cells, different studies using virtual cells also require the set-up of optimal extracellular conditions. This can be done easily by the user setting the ranges of the activity (from 0 to 100%) of the individual extracellular (e.g., external) species via user inputs (e.g., provided via sliders of a graphical interface or via typing appropriate activity levels in appropriate text boxes). In our exemplary study, because the user is interested in the effects of EGF on the virtual cell, the activity of EGF is set to range on the full scale between 0 and 100% ON. On the other hand, the activity ranges of the remaining external species are selected for optimal results based on previous research and backed by laboratory-generated data. For instance, the Extracellular Matrix (ECM) is set to higher activity levels, varying between 56 and 100%. This corresponds to a biological finding that EGF-induced growth, as well as other cellular processes, is dependent on cell anchorage via ECM. With large scale models, while optimal conditions should be determined, the simulations and results are not sensitive to exact values. Users can specify the number of simulations to be ran within the study. During each simulation, an activity level for each extracellular species is selected randomly by the software of the system 100 such that the activity level falls within the specified range. As a result, the user is able to simulate what would amount to many different laboratory experiments, with each experiment corresponding to a different external condition.

Once the in silico experiment has completed, users can start generating their analyses. The dynamic analysis tool (e.g., ChemChains) 116 allows users to generate dose-response curves to investigate qualitative (e.g., input-output) relationships between external cellular signals and various components of the virtual cell, such as the one between EGF and Akt. An additional significant advantage of computational experiments using the dynamical analysis tool 116 is that users can generate a number of analyses without re-running the entire experiment. For instance, in addition to examining the functional relationship of Akt and growth, one can generate similar dose-response curves for any species in the model using the one multi-simulation experiment. This can be done by specifying the appropriate external and output species from menus (e.g., drop-down menus) available on the page. Further, similar to the real time simulation feature, mutations to any of the cellular species can be easily specified which allows users to simulate gain/loss-of-function in an intuitive fashion.

Dynamical analysis simulations can be used not only to generate new hypotheses, but also to test the correctness of the model. Because the models are built using local knowledge of the individual interactions, the correctness of the model is tested on global phenomena of the biological system. The above example demonstrates how the model of signal transduction in a fibroblast cell can be tested to ensure that species associated with apoptosis and growth (such as Akt) appropriately respond to a growth signal (such as EGF). If the dose-response curve for Akt and EGF suggested a negative correlation, one would have to go back and investigate which of the local interaction data resulted in the contradictory result.

Supporting Modules

In embodiments, the memory 106 includes a fourth module (e.g., a user management module, user management subsystem) 118. The user management module 118 is configured for authenticating and authorizing users of the system. For example, the user management module 118 manages who can and who cannot access the software and what user privileges are granted once logged in.

In embodiments, the memory 106 includes a fifth module (e.g., a model management module, model management subsystem) 120. The model management module 120 is configured for keeping all models organized and available to the users. The system 100 is configured for supporting public models and private models. Public models are available to the entire user community for simulations. Although all users can provide input on the models' components and the logic of each component's regulatory mechanism, only administrators can make direct changes to public models. This is to prevent chaotic model changes, as well as to ensure that stable versions of public models are available to all users. However, users can download any public model to the user's sandbox, which allows them to modify and simulate in an isolated environment. This is particularly useful if a user wants to play with a given public model, perhaps add his/her own laboratory data and based on the updated model, suggest their changes to the administrator of the public model. Conversely private models are models visible only to users that create these models. Private models are created and organized by the model management subsystem 120 in user's sandbox, where they can also be modified, simulated and analyzed in any way desired. In addition, users can also share models in their sandbox with multiple collaborators. Sharing of the models is implemented on multiple levels to give users and collaborators maximum flexibility in managing their models. Options provided include: i) a create-copy option, which allows users to create a copy of their collaborator's model for further modifications and simulations in their own sandbox; ii) a read-only option, which allows users' collaborators to see each other's models, but does not allow copying of the model or changing of the model's contents; and iii) a write option, which allows users' collaborators to modify the model and work collaboratively on creating larger and more accurate models.

Collaboration and Accessibility

As mentioned above, promoting enhanced collaboration amongst laboratory scientists working in different areas of complex biological/biochemical processes and promoting enhanced accessibility of modeling frameworks to these laboratory scientists are key characteristics of the system 100 described herein. As mentioned above, published models, created by the community, are accessible to all registered users, fostering the idea of open science. All users can view the bio-logic, as well as the information in the knowledge base module 112, and perform real time simulations on these published models directly. To make changes to the published models and to see how these modifications affect the dynamics of the model, all users can create personal copies of published models. Once a copy of a published model is created, the copy can be made available and visible to only the one user.

In embodiments, a user can create a collection of models and can designate a select group of colleagues with which the user wishes to share and collaborate on these models. The degree to which such a collaboration can take place is guided by the choice of multiple (e.g., three) types of permission a user can specify when sharing his/her model. First, models can be shared such that other users can simulate the shared models and view the bio-logic of the shared models. A second way of model sharing also allows other users to contribute to the models directly and edit them. Finally, models can also be shared so that other users become model administrators and have the same rights as the creator of the model, including the ability to share the model with additional collaborators. In addition to being able to share models with any and every user of the system (e.g., platform) 100, features to export models in formats that can work with other modeling tools are also available. In embodiments, users can export all mathematical expressions for each model, including the available published models. Systems Biology Markup Language (SBML) is a format which provides the ability to exchange the models in an effective fashion. In embodiments, the system (e.g., platform, cell collective, modeling suite) 100 is configured for providing a forum which allows users to communicate with the scientific community, as well as with the platform's development team.

In embodiments, the system (e.g., platform) 100 implements an open source database communication framework (e.g., Hibernate) by implementing Data Access Objects (DAOs) which are specific to the communication framework (e.g., Hibernate-specific DAOs). Further, an open-source platform framework (e.g., Spring) which can be used with any Java application can also be implemented. In embodiments, these frameworks are added to all subsystems of the platform.

As mentioned above, Bio-Logic Builder 114 defines a relatively small number of qualitative biological building blocks that the user can use to build a computational model. With this tool, complex mathematical models can be built even by users with no mathematical training, and no biological parameters (e.g., rate constants) are required. The graphical user interface (GUI) for the Bio-Logic Builder 114 is user-friendly.

In embodiments, the system 100 includes save/load/export/import features. A save and load feature included in the system 100 allows for users to revisit their simulations at a later time. Further, the system 100 allows for each user to have their own folder with sub-folders dedicated to each of the users' simulation experiments. Within these folders, necessary raw data for reconstructing the users' real time simulation graphs is included. To be able to load the simulation data and graph it at a later time, the information about the simulation experiments (e.g., simulation name, date/time, directory path) will be stored in the memory (e.g., main database) 106 of the system 100 (e.g., platform) so that the program can locate where to search for the raw data when the user requests it. The export function allows users to save data locally (e.g., on the external system(s)) 110 by allowing the user to export the simulation data in several file formats, such as tab-delimited text. Simulation results can be generated as tab-delimited text files. The import function allows users to import data from their computer 110 to the platform 100. When initiated, the import function triggers the creation of a new simulation directory structure, moves the data to the appropriate directories and writes the necessary information to the database 106.

In embodiments, the dynamic analysis tool (e.g., Chem-Chains) 116 provides automated large-scale analyses to find patterns of extracellular environmental cues and the corresponding output signal patterns used to conduct input-output mapping studies. In embodiments, the user accesses this feature via a graphical user interface (GUI) of the dynamic analysis tool (e.g., ChemChains) 116 through selection of a menu option. The GUI of the dynamic analysis tool (e.g., ChemChains) 116 is configured for inquiring a user to provide information such as different activity levels of the models' external species (e.g., drugs, receptor expressions, etc.) necessary for simulation. The dynamic analysis tool (e.g., ChemChains) 116, via appropriate Java business logic, performs processing and simulations for this data. The experiment data is stored on the server and is easily accessible to a user.

In embodiments, the system 100 provides a mechanism by which the community of laboratory scientists can collaborate and contribute their intimate knowledge of local interactions into a large-scale global model for promoting the creation of larger and more accurate models. Further, as discussed above, the system 100 allows the scientists to communicate their data in qualitative terms for creating dynamic models, so that the scientists do not have to directly interact with the model's mathematical complexities.

An Exemplary Process for Providing Dynamic Modeling via the System

Figure 3A:
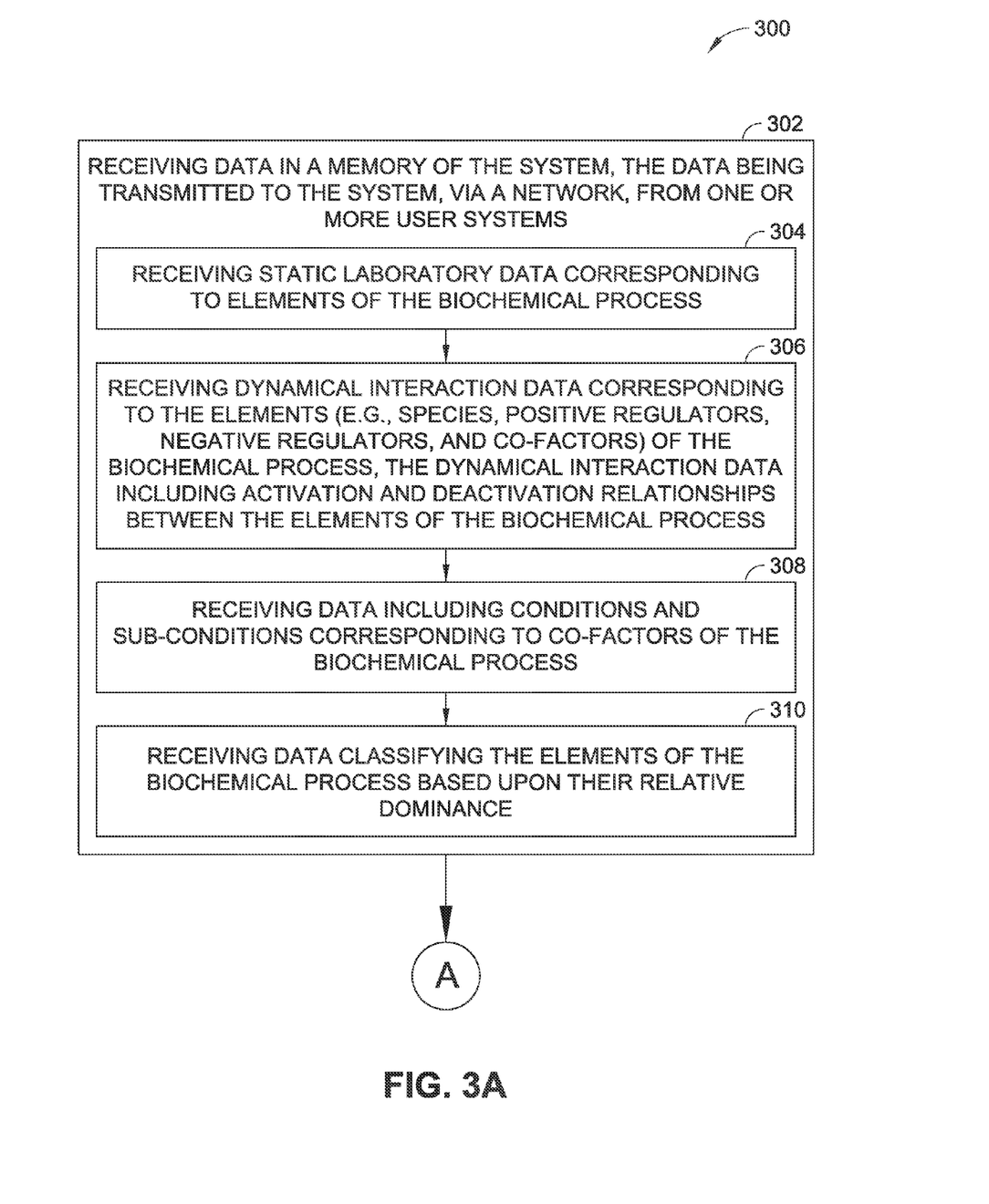
FIGS. 3A and 3B depict a flow chart illustrating a method for dynamic modeling of biochemical processes using the system shown in FIGS. 1 and 2.
Figure 3B:
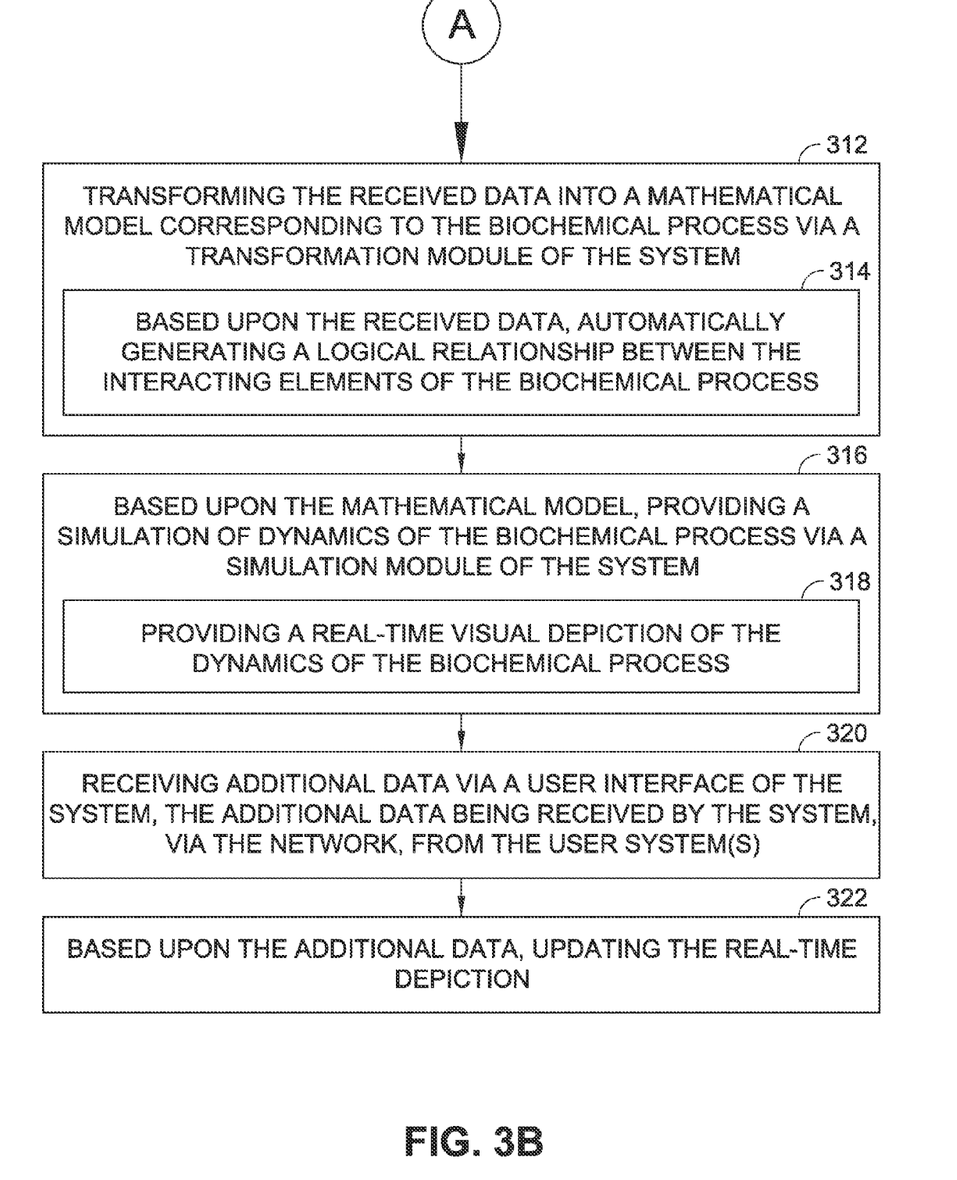

FIGS. 3A and 3B depict a flowchart illustrating a method for providing dynamic modeling of a biological and/or biochemical process via the system 100 shown in FIGS. 1 and 2. The method 300 includes the step of receiving data in a memory of the system, the data being transmitted to the system, via a network, from one or more user systems 302. In embodiments, the step of receiving data 302 further includes the step of receiving laboratory data corresponding to elements of the biochemical process 304. In embodiments, the step of receiving data 302 further includes the step of receiving dynamical interaction data corresponding to the elements of the biochemical process 306. For example, the dynamical interaction data includes activation and deactivation relationships between the elements of the biochemical process. Further, the elements can include one or more of: species, positive regulators, negative regulators and co-factors.

In embodiments, the step of receiving data 302 further includes the step of receiving data including conditions and sub-conditions corresponding to co-factors of the biochemical process 308. For example, a drag-and-drop menu of the user interface of the system 100 can be implemented by the user for defining positive and negative regulators and/or conditions and sub-conditions. In embodiments, the step of receiving data 302 further includes the step of receiving data classifying the elements of the biochemical process based upon their relative dominance 310.

In embodiments, the method 300 further includes the step of transforming the received data into a mathematical model corresponding to the biochemical process via a transformation module of the system 312. In embodiments, the step of transforming the laboratory data into a mathematical model 312 further includes the step of based upon the received data, automatically generating a logical relationship between the interacting elements of the biochemical process 314.

In embodiments, the method 300 further includes the step of, based upon the mathematical model, providing a simulation of dynamics of the biochemical process via a simulation module of the system 316. For example, the mathematical model can correspond to a virtual cell. In embodiments, the step of providing a simulation of dynamics of the biochemical process 316 further includes the step of providing a real-time visual depiction of the dynamics of the biochemical process 318.

In embodiments, the method 300 further includes the step of receiving additional data via a user interface of the system, the additional data being transmitted to the system, via the network, from the one or more user systems 320. In embodiments, the method 300 further includes, based upon the additional data, updating the real-time visual depiction 322. Users can interact with the model in real-time to see the effects of changing parameters in the cellular environment on the simulated model and the species included in the model. For instance, the user interface or sliders of the user interface may be implemented for allowing users to change the amount of species and/or molecules that are external to the model and/or to add mutations that allow users to specify components of the model to be either completely active or inactive. These changes can be made during simulations so that users can see their effects on the model. Further, user inputs can be received for pausing and resuming a simulation.

It is to be noted that the foregoing described embodiments may be conveniently implemented using conventional general purpose digital computers programmed according to the teachings of the present specification, as will be apparent to those skilled in the computer art. Appropriate software coding may readily be prepared by skilled programmers based on the teachings of the present disclosure, as will be apparent to those skilled in the software art.

It is to be understood that the embodiments described herein may be conveniently implemented in forms of a software package. Such a software package may be a computer program product which employs a non-transitory computer-readable storage medium including stored computer code which is used to program a computer to perform the disclosed functions and processes disclosed herein. The computer-readable medium may include, but is not limited to, any type of conventional floppy disk, optical disk, CD-ROM, magnetic disk, hard disk drive, magneto-optical disk, ROM, RAM, EPROM, EEPROM, magnetic or optical card, or any other suitable media for storing electronic instructions.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for providing dynamic modeling of a biochemical process via a system, the method comprising:
    receiving data in a memory of the system, the data being transmitted to the system, via a network, from a plurality of user systems including at least a first user system and a second user system;
    transforming the received data into a mathematical model corresponding to the biochemical process via a transformation module of the system;
    based upon the mathematical model, providing a simulation of dynamics of the biochemical process via a simulation module of the system;
    publishing the mathematical model to an interactive database, wherein the interactive database receives a first update from the first user system and a second update from the second user system via the network;
    based upon the first update and the second update, providing a modified real-time simulation of dynamics of the biochemical process for the plurality of user systems via the simulation module; and
    updating the published mathematical model based upon the modified real-time simulation.

2. The method as claimed in claim 1, wherein the step of receiving data further includes the step of:
    receiving laboratory data corresponding to elements of the biochemical process; and
    receiving dynamical interaction data corresponding to the elements of the biochemical process.

3. The method as claimed in claim 2, wherein the dynamical interaction data includes activation and deactivation relationships between the elements of the biochemical process.

4. The method as claimed in claim 2, wherein the elements include at least one of: species, positive regulators, negative regulators, and co-factors.

5. The method as claimed in claim 2, wherein the step of receiving data further includes the step of:
    receiving data including conditions and sub-conditions corresponding to co-factors of the biochemical process; and
    receiving data classifying the elements of the biochemical process based upon their relative dominance.

6. The method as claimed in claim 5, wherein the step of transforming the laboratory data into a mathematical model further includes the step of:
    based upon the received data, automatically generating a logical relationship between the elements of the biochemical process.

7. The method as claimed in claim 6, wherein the step of providing a simulation of dynamics of the biochemical process further includes the step of:
    providing a real-time visual depiction of the dynamics of the biochemical process.

8. The method as claimed in claim 7, further comprising:
    receiving additional data via a user interface of the system, the additional data being transmitted to the system, via the network, from at least one of the user systems; and
    based upon the additional data, updating the real-time visual depiction.

9. The method as claimed in claim 8, wherein the additional data includes one of: a command to change an amount of one or more of the elements, a command to change a type of one or more of the elements, and a command to change an activity level of one or more of the elements.

10. The method as claimed in claim 8, wherein the additional data includes a command to one of: pause the simulation or resume the paused simulation.

11. The method as claimed in claim 5, wherein positive regulators, negative regulators, conditions and sub-conditions are definable by a user via a drag-and-drop menu provided via the user interface of the system.

12. A non-transitory computer-readable medium having computer-executable instructions for performing a method for providing dynamic modeling of a biochemical process via a system, the method comprising:
    receiving data in a memory of the system, the data being transmitted to the system, via a network, from a plurality of user systems including at least a first user system and a second user system;
    transforming the received data into a mathematical model corresponding to the biochemical process via a transformation module of the system;
    based upon the mathematical model, providing a simulation of dynamics of the biochemical process via a simulation module of the system;
    publishing the mathematical model to an interactive database, wherein the interactive database receives a first update from the first user system and a second update from the second user system via the network;
    based upon the first update and the second update, providing a modified real-time simulation of dynamics of the biochemical process for the plurality of user systems via the simulation module; and
    updating the published mathematical model based upon the modified real-time simulation.

13. The non-transitory computer-readable medium as claimed in claim 12, wherein the step of receiving data further includes the step of:
    receiving laboratory data corresponding to elements of the biochemical process; and
    receiving dynamical interaction data corresponding to the elements of the biochemical process.

14. The non-transitory computer-readable medium as claimed in claim 13, wherein the dynamical interaction data includes activation and deactivation relationships between the elements of the biochemical process.

15. The non-transitory computer-readable medium as claimed in claim 14, wherein the elements include at least one of: species, positive regulators, negative regulators, and co-factors.

16. The non-transitory computer-readable medium as claimed in claim 15, wherein the step of receiving data further includes the step of:
    receiving data including conditions and sub-conditions corresponding to co-factors of the biochemical process; and
    receiving data classifying the elements of the biochemical process based upon their relative dominance.

17. The non-transitory computer-readable medium as claimed in claim 16, wherein the step of transforming the laboratory data into a mathematical model further includes the step of:
    based upon the received data, automatically generating a logical relationship between the elements of the biochemical process.

18. The non-transitory computer-readable medium as claimed in claim 16, wherein the step of providing a simulation of dynamics of the biochemical process further includes the step of:

provide a real-time visual depiction of the dynamics of the biochemical process.

19. The non-transitory computer-readable medium as claimed in claim 18, the method further comprising:

receiving additional data in the memory of the system via a user interface of the system, the additional data being transmitted to the system, via the network, from at least one of the user systems; and based upon the additional data, updating the real-time visual depiction.

20. A system for providing dynamic modeling of at least one of a biochemical process or a biological process, comprising:

a processor;

a network interface, the network interface configured for connecting the system to a plurality of user systems including at least a first user system and a second user system via a network;

a memory having computer executable instructions stored thereon, the computer executable instructions configured for execution by the processor to:

receive data in the memory of the system, the data being transmitted to the system, via the network, from one or more user systems included in the plurality of user systems, the data corresponding to elements of the at least one of the biochemical process or the biological process, the elements including at least one of: species, regulators and co-factors, the data including interaction data for the elements, the interaction data including activation and deactivation relationships between the elements, the data further including conditions and sub-conditions corresponding to co-factors of the at least one of the biochemical process or the biological process, the received data further including data classifying the elements based upon their relative dominance;

transform the received data into a mathematical model corresponding to the at least one of the biochemical process or the biological process via a transformation module of the system, including automatically generating a logical relationship between the elements of the at least one of the biochemical process or the biological process;

based upon the mathematical model, provide a simulation of dynamics of the at least one of the biochemical process or the biological process via a simulation module of the system including providing a real-time visual depiction of the dynamics of the at least one of the biochemical process or the biological process;

publish the mathematical model to an interactive database, wherein the interactive database receives a first update from the first user system and a second update from the second user system via the network; and based upon the first update and the second update, provide a modified real-time simulation of dynamics of the at least one of the biochemical process or the biological process for the plurality of user systems via the simulation module; and updating the published mathematical model based upon the modified real-time simulation.

\* \* \* \* \*